US012262908B2

(12) United States Patent
Collinson et al.

(10) Patent No.: US 12,262,908 B2
(45) Date of Patent: Apr. 1, 2025

(54) APPARATUS AND METHOD FOR REMOVAL OF INTRAUTERINE FIBROID FORMATIONS

(71) Applicant: Caldera Medical, Inc., Agoura Hills, CA (US)

(72) Inventors: Mike Collinson, Agoura Hills, CA (US); Manish Vaishya, Agoura Hills, CA (US); Jose Luis Charvet, Agoura Hills, CA (US)

(73) Assignee: Caldera Medical, Inc., Westlake Village, CA (US)

(*) Notice: Subject to any disclaimer, the term of this patent is extended or adjusted under 35 U.S.C. 154(b) by 546 days.

(21) Appl. No.: 16/799,711

(22) Filed: Feb. 24, 2020

(65) Prior Publication Data
US 2020/0268404 A1 Aug. 27, 2020

Related U.S. Application Data

(60) Provisional application No. 62/809,456, filed on Feb. 22, 2019.

(51) Int. Cl.
*A61B 17/32* (2006.01)
*A61B 17/42* (2006.01)

(52) U.S. Cl.
CPC ........ *A61B 17/32002* (2013.01); *A61B 17/42* (2013.01); *A61B 2017/320028* (2013.01); *A61B 2017/320032* (2013.01); *A61B 2017/4225* (2013.01); *A61B 2560/0214* (2013.01)

(58) Field of Classification Search
CPC .............. A61B 17/32002; A61B 17/42; A61B 2017/320028; A61B 2017/320032; A61B 2017/4225; A61B 2560/0214; A61B 2017/4216
See application file for complete search history.

(56) References Cited

U.S. PATENT DOCUMENTS

| | | | | |
|---|---|---|---|---|
| 2002/0055689 | A1* | 5/2002 | Kaplan | A61B 10/0233 600/567 |
| 2009/0270812 | A1* | 10/2009 | Litscher | A61M 1/842 604/164.01 |
| 2011/0036890 | A1 | 2/2011 | Ma | |
| 2011/0073342 | A1* | 3/2011 | Gilsdorf | A61B 17/00 173/217 |
| 2012/0109007 | A1 | 5/2012 | Rhad et al. | |
| 2014/0171998 | A1 | 6/2014 | Riva | |
| 2014/0276210 | A1 | 9/2014 | O'Sullivan et al. | |

OTHER PUBLICATIONS

WIPO, U.S. International Search Authority, International Search Report and Written Opinion mailed Jun. 12, 2020 in International Patent Application No. PCT/US2020/019550, 10 pages.

* cited by examiner

*Primary Examiner* — Ashley L Fishback
*Assistant Examiner* — Chima U Igboko
(74) *Attorney, Agent, or Firm* — Inskeep IP Group, Inc.

(57) ABSTRACT

A drive system for a tissue resection device that drives a cutting tube in a rotating and reciprocating motion simultaneously. The cutting tube moves within an outer tube having a window at a distal end thereof. When activation of the device ceases, the device remains powered until the cutting tube assumes an extended position, thereby closing the window.

18 Claims, 7 Drawing Sheets

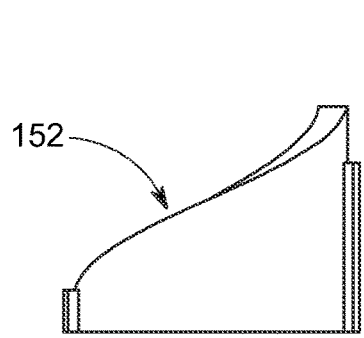
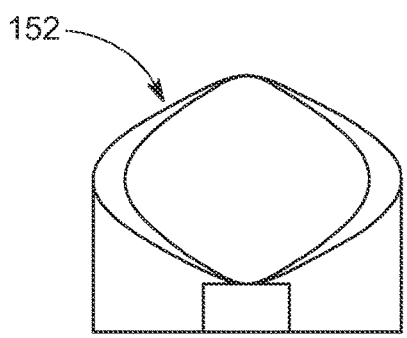
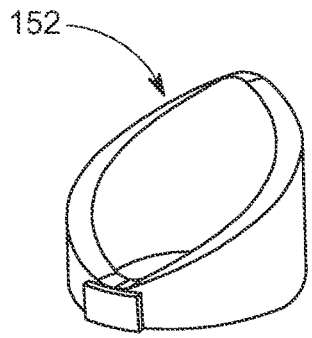
FIG. 5A  FIG. 5B  FIG. 5C
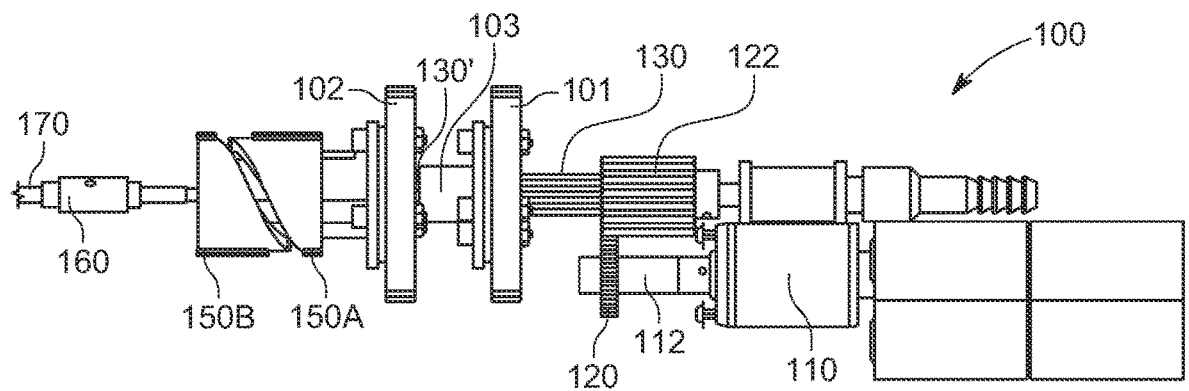
FIG. 6

APPARATUS AND METHOD FOR REMOVAL OF INTRAUTERINE FIBROID FORMATIONS

RELATED APPLICATIONS

This application claims priority to U.S. Provisional Application Ser. No. 62/809,456 filed Feb. 22, 2019 entitled Apparatus and Method for Removal of Intrauterine Fibroid Formations, which is hereby incorporated herein by reference in its entirety.

FIELD OF THE INVENTION

The present invention relates to the field of uterine tissue resection and, more particularly, to instruments for the removal of uterine tissue and methods of use thereof.

BACKGROUND OF THE INVENTION

Uterine tissue resection tools are employed for the intrauterine removal of polyps, fibroids and myomas. For intrauterine removal of polyps, fibroids and myomas, the existing removal devices have limited effectiveness to cut tissue, due to the driving mechanisms that are used. For high mobility, improved drive mechanisms and effective methods of transfer of the drive mechanism to the cutter are needed.

OBJECTS AND SUMMARY OF THE INVENTION

The aforementioned needs are met by the various embodiments of the present invention, which provides improved drive mechanisms for powering a cutting instrument for intrauterine tissue resection.

One aspect of the invention provides a reciprocating drive system for a cutting tube that includes a power source, a motor connected to the power source and having a drive shaft extending therefrom, a first spur gear attached to the drive shaft, a worm connected to the drive shaft, a cutting tube adjacent the drive shaft and parallel thereto, a second spur gear surrounding the cutting tube and meshed with the first spur gear, a worm gear positioned under the worm and meshed therewith such that rotation of the worm around a first axis results in rotation of the worm gear around a second axis perpendicular to the first axis and a crank attached at one end to the worm gear and at a second end to a collar attached to the cutting tube. Rotation of the drive shaft causes rotation of the cutting tube via the first and second spur gears and simultaneously causes reciprocating translation of the cutting tube along a longitudinal axis thereof.

In another aspect the reciprocating drive system also includes a first switch connected to a toggle and electrically located between the power source and the motor such that the motor cannot receive current from the power source unless the first switch is closed.

In one embodiment there is a second switch connected to an activation button and electrically located between the first switch and the motor such that the motor cannot receive current from the power source unless the first switch and second switches are closed. In one embodiment the second switch is closed by depressing the activation button.

In another embodiment there is a third switch electrically located between the first switch and the motor such that the motor cannot receive current from the power source unless the first switch and at least one of the second and third switches are closed. The third switch may be biased closed and is opened by a sleeve attached to the cutting tube and reciprocating therewith. The sleeve is positioned on the cutting tube and relative to the third switch such that the third switch is opened with the cutting tube is in an extended position.

Another aspect of the invention provides a method of resecting tissue. The method involves introducing a shaft of a tissue resection device into a target area, the shaft having a closed distal end, a first lumen extending through the shaft and ending proximal the distal end, the lumen carrying a cutting tube therein, the cutting tube attached to a drive system that simultaneously rotates and reciprocates the cutting tube within the shaft. The tissue to be resected is drawn into a window formed in the side of the shaft by applying suction to a second lumen that extends through the cutting tube. The tissue is resected by allowing the suction to hold the tissue in the window as the cutting tube translates from a retracted position in which the window is unobstructed to an extended position in which the cutting tube blocks the window, the tissue being cut by relative movement between a distal end of the cutting tube and an edge of the window.

In one aspect, introducing the shaft of the tissue resection device into the target area comprises inserting the shaft through the working channel of a hysteroscope.

In another aspect, the method further includes stopping suction to the window after a desired amount of tissue has been resected. Stopping suction to the window may be accomplished by placing the cutting tube in the extended position, thereby blocking the window.

In one aspect, placing the cutting tube in the extended position is performed by releasing an activation button supplying current to a motor driving the cutting tube resulting in all current to the motor flowing through a safety switch that opens only when the cutting tube is in the extended position.

Another aspect of the invention pertains to a tissue resection device that comprises a power source; a single motor connected to the power source; an outer tube having a first lumen, a closed distal end, and a window through a sidewall thereof leading to the lumen, the window being located proximal of the closed distal end; and an inner tube within the first lumen and having a second lumen extending between an open distal end and an open proximal end, wherein the open proximal end is connected to a suction source. The inner tube is connected to the motor such that when the single motor receives current from the power source, the inner tube rotates and reciprocates simultaneously within the outer tube.

In one aspect, the device includes a first mechanism connecting the single motor and the inner tube that transfers rotational movement from a drive shaft of the single motor to the inner tube.

In another aspect, the first mechanism comprises a first spur gear attached to the drive shaft and a second spur gear attached to the inner tube, wherein the first spur gear is meshed with the second spur gear.

One embodiment includes a second mechanism connecting the single motor and the inner tube that converts rotational movement from a drive shaft of the single motor into reciprocating movement of the inner tube. The second mechanism may be a worm attached to the drive shaft and a worm gear attached to the inner tube via a crank.

In one embodiment, the crank has a first end attached to the worm gear and a non-centric location and a second end attached to a collar on the inner tube.

In one aspect, the device includes a first switch and a second switch electrically connected in series between the power source and the single motor.

In one aspect, the device also has a third switch connected in parallel with the second switch between the first switch and the single motor.

In one aspect of the invention, a drive mechanism is provided that includes a motor and a gearing mechanism allows the rotating motor to both rotate and translate a single inner cutter tube within an outer, stationary cutter tube.

In certain embodiments, the worm gear drive assembly provides a relatively more compact system due to the presence of lesser parts on its gear train as compared to the planetary gear drive assembly. Therefore, it costs less and has lesser issues between mating parts. In some preferred embodiments, a small housing is needed to encase the worm gear drive assembly as compared to the planetary gear drive assembly.

In certain embodiments of the present invention, a portable device with a mechanical cutter is employed to cut and remove the polyps and fibroids from the uterus. The power is supplied for the cutter electrically, typically using an onboard battery or an external power source to drive a motor and create a high-speed rotary motion, for example, typically between 4,000 and 12,000 revolutions per minute.

In certain embodiments, the present invention provides mobility and ease of use, lower transmitted vibrations, and low capital cost. In some embodiments, the present invention also facilitates in-office use and provides more freedom in defining linear motion profiles.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which

FIG. 5a is a right-side elevation of an embodiment of a cam of the invention;

FIG. 5b is a front elevation of an embodiment of a cam of the invention;

FIG. 5c is a left-side elevation of an embodiment of a cam of the invention;

FIG. 6 is a side elevation of an embodiment of a drive system of the invention;

DESCRIPTION OF EMBODIMENTS

Figure 1:
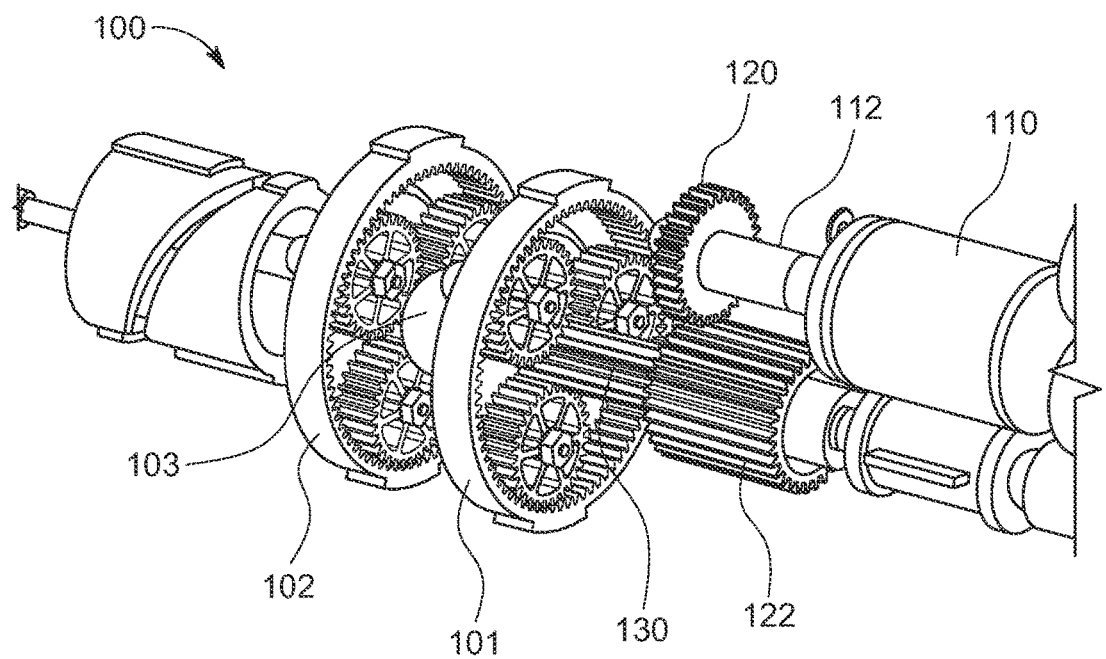
FIG. 1 is a perspective view of an embodiment of a planetary gear assembly of the invention.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The present invention is directed to drive assemblies for uterine tissue resectors. The uterine tissue resector is a dual-lumen, tissue cutting instrument capable of removing and irrigating tissues from the uterus. The dual lumen cutting tube assembly comprises an inner cutting tube with a cutting window near a distal end and an outer cutting tube with a cutting window near a distal end. The uterine tissue resector employs a rotational and longitudinal reciprocating cutting action by rotating and longitudinally translating the inner cutting tube relative to the outer cutting tube, the outer cutting tube being statically attached to a handle or housing of the resector.

The uterine tissue resectors driven by the drive assemblies of the present invention are designed for, and may be used with, the working channels of a hysteroscope. An example of a hysteroscope with which the present invention may be used, is described in U.S. Patent Pub. No. 2019/0133640 by Charvet et al., filed Nov. 9, 2018, entitled Rotary Instruments And Methods For Intrauterine Tissue Resection, incorporated by reference herein.

According to the present invention, the inner cutting tube is attached to a motor. When the motor is activated, the inner cutting tube rotates around a central axis as well as moves longitudinally in a reciprocating or distal-and-proximal motion. The present invention discloses various resector drive assemblies, for example, 1) a planetary gear drive assembly, 2) a worm gear drive assembly and 3) a spur gear drive assembly, for providing the rotational and longitudinal reciprocating cutting action.

Detailed elements of the planetary gear drive assembly according to the present invention are disclosed in FIGS. 1-7. Referring to FIG. 1, a planetary gear drive assembly 100 includes a motor 110, a drive shaft 112 attached at one end to the motor 110 and at another end to a drive gear 120. The drive gear 120 is positioned adjacent to and meshed with a spur gear 122. The assembly 100 further employs a first planetary gear 101 and a second planetary gear 102. A driver 130 extends from the spur gear 122 at one end and interfaces with the first planetary gear 101.

Figure 2:
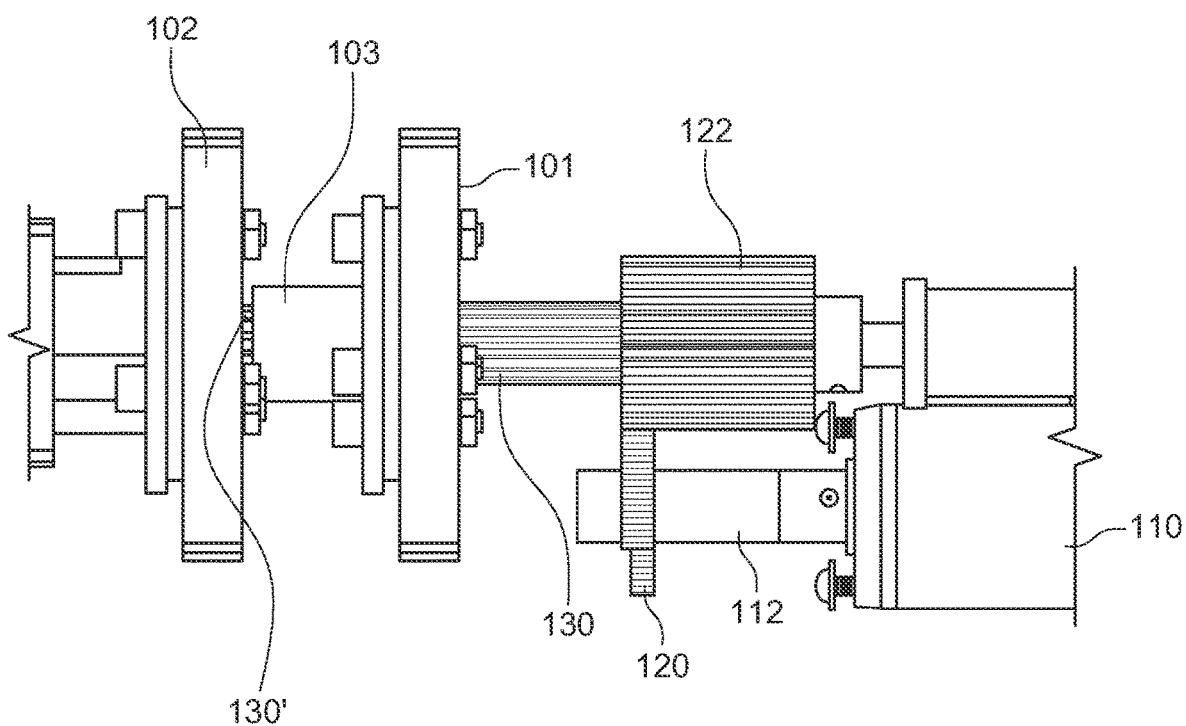
FIG. 2 is a side elevation of an embodiment of a planetary gear assembly of the invention.

FIG. 2 is an side view of the planetary gear drive assembly 100 disclosed in FIG. 1 and includes the first planetary gear 101 and a second planetary gear 102, a motor 110, a drive shaft 112 attached at one end to the motor 110 and at an opposite end to a drive gear 120, spur gear 122 and driver or sun gear 130.

Figure 3:
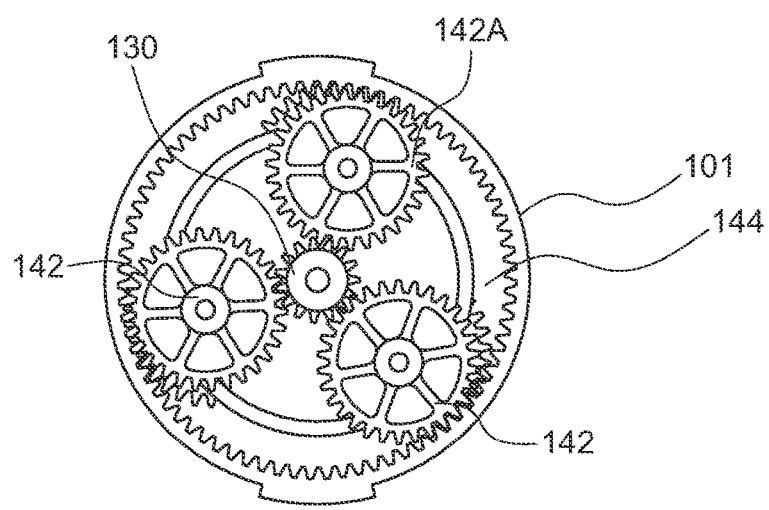
FIG. 3 is an end view of an embodiment of a planetary gear assembly of the invention.

FIG. 3 shows an end view of the planetary gears employing the central sun gear or driver 130 surrounded by and meshed with three planet gears and the three planet gears meshed with an encircling ring gear.

Figure 4:
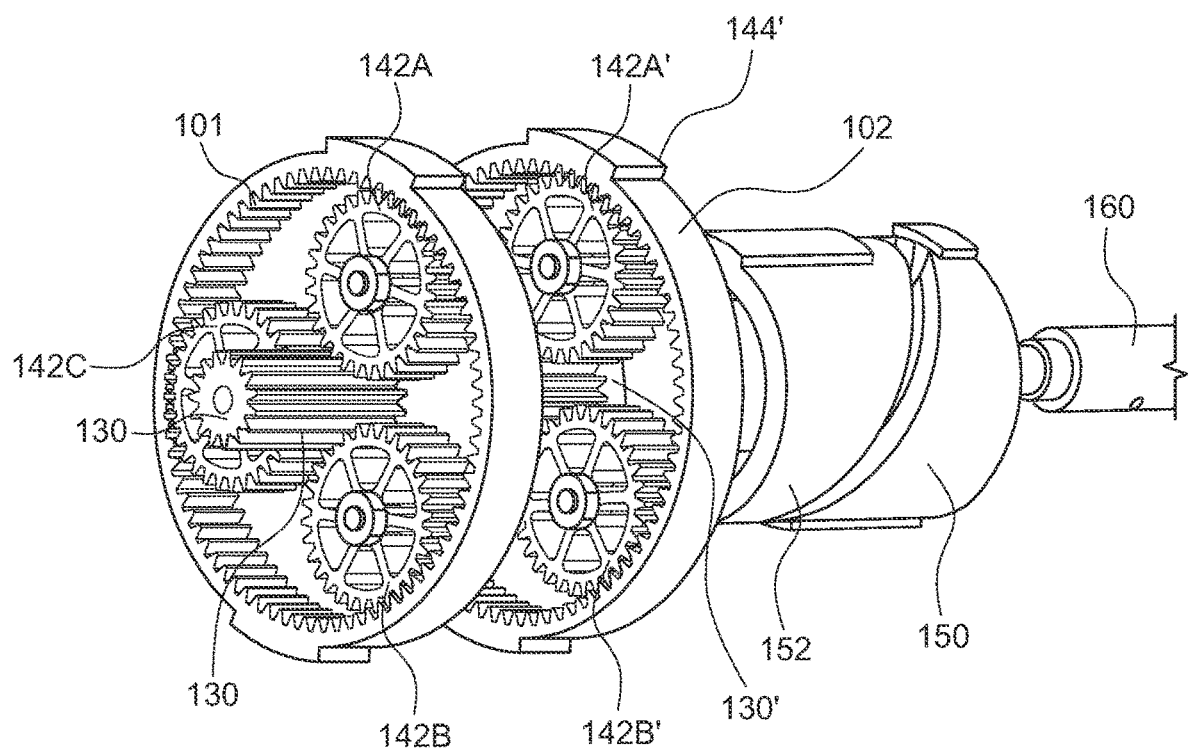
FIG. 4 is a perspective view of an embodiment of a planetary gear assembly of the invention.

FIG. 4 illustrates the first planetary gear 101 and second planetary gear 102 and a cam assembly 150 attached next to the second planetary gear 102. The cam assembly 150 employs groove 152 and is further attached to a follower 160. As can be seen from FIG. 4, the first planetary gear 101 comprises three planet gears 142A, 142B and 142C surrounding driver 130 which serves as a sun gear. A ring gear 144 (FIG. 3) surrounds the planet gears. The sun gear 130 meshes with each of the planet gears (142A, 142B and 142C) and each of the planet gear meshes with the ring gear 144. The second planetary gear 102 further comprises planet gears 142A', 142B' and 142C'. Referring further to FIGS. 1, 2 and 4, the planet gears 142A, 142B, and 142C connect to the central sun gear 130' of the second planetary gear 102 through the carrier 103 to effect a desired two-stage speed reduction. The central sun gear 130 drives the first planetary gear 101 and meshes with the planet gears 142A', 142B' and 142C'. A ring gear 144' encompasses the planet gears.

Figure 7:
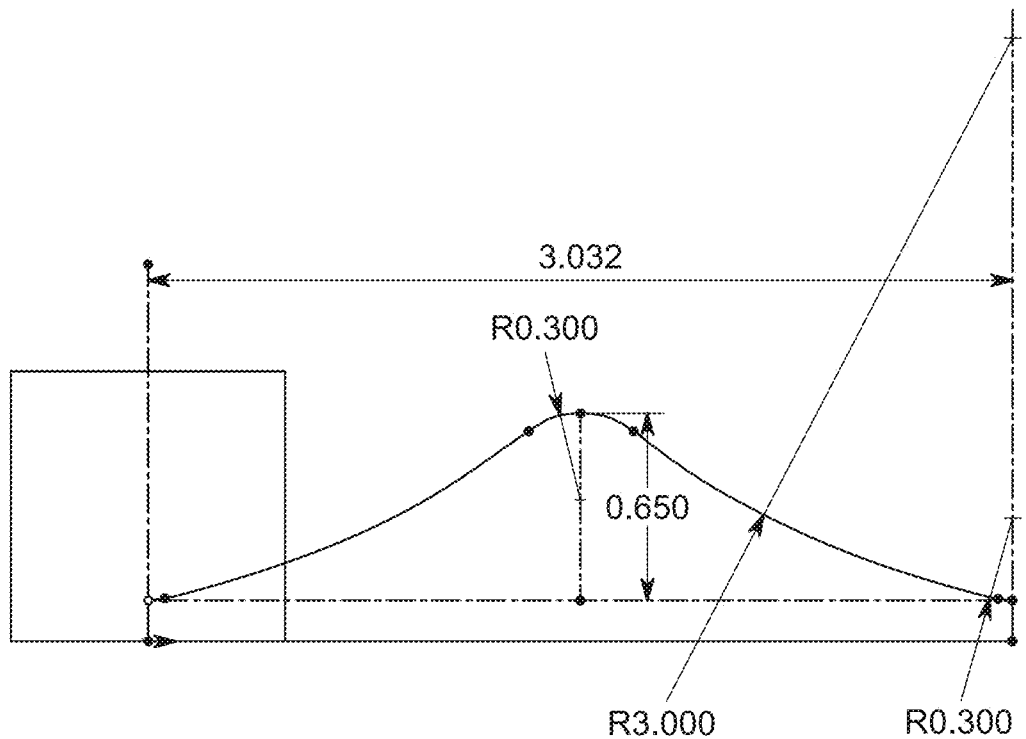
FIG. 7 is a graphical representation of a path created by rotation of the embodiment of the cam assembly of FIGS. 5a-5c.
Figure 12:
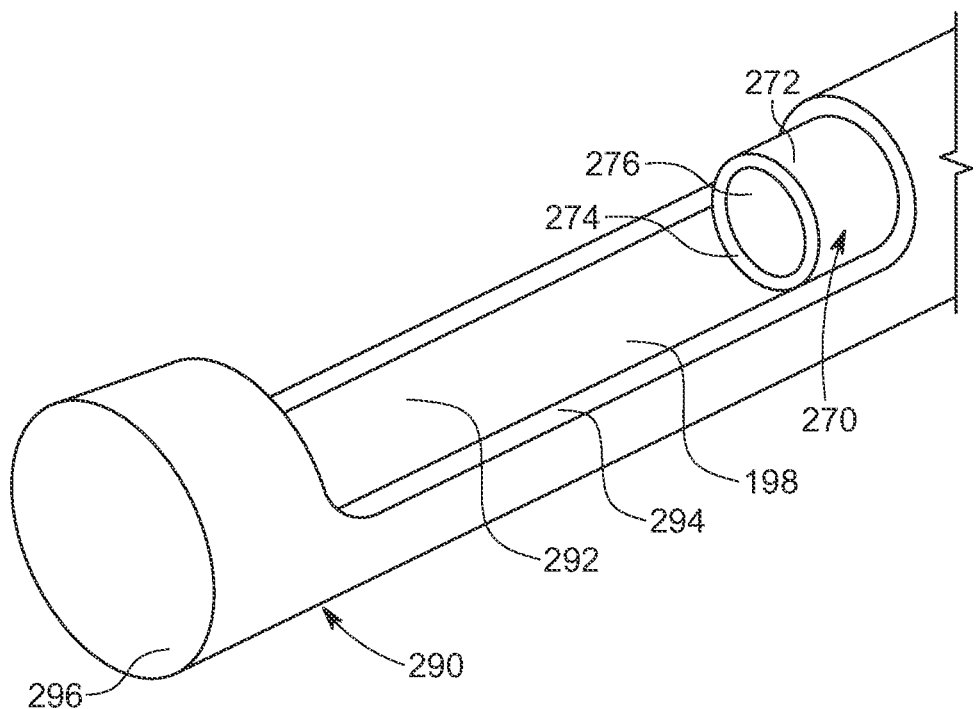
FIG. 12 is a perspective view of an embodiment of a distal end of the apparatus of the invention close to a retracted position; and, FIG. 13 is a perspective view of an embodiment of a distal end of the apparatus of the invention in an extended position.
Figure 13:
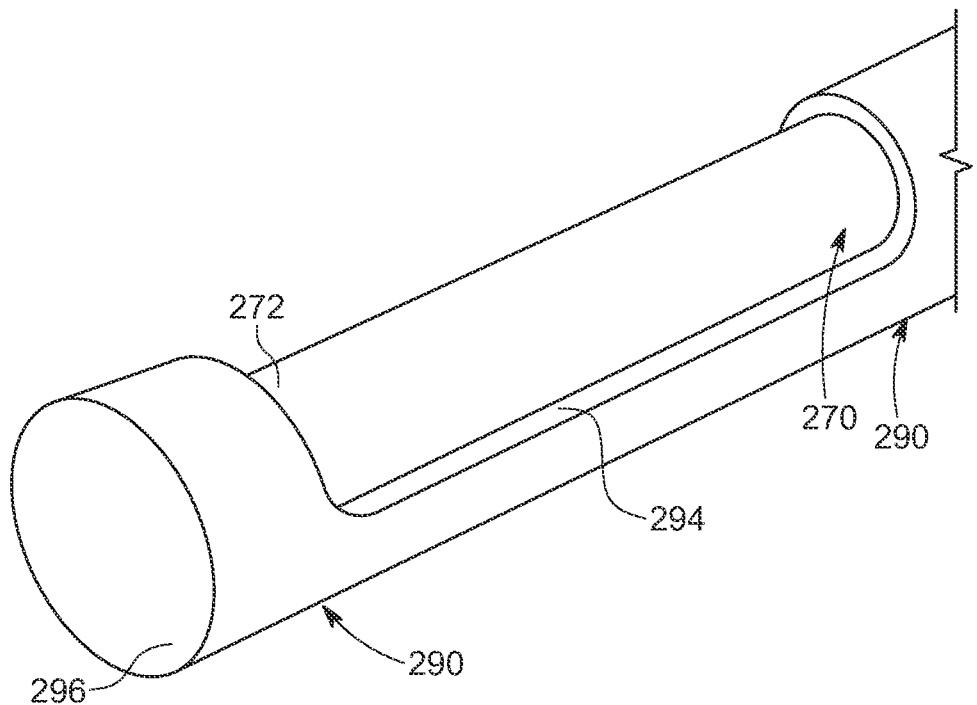

FIGS. 5A-5C are depictions of details of the groove 152 of cam 150, which is responsible for imparting a reciprocating motion to a cutter tube 170 extending from the drive system 100, and which ultimately resects the tissue at a distal end of the device (not shown in this embodiment but may be identical to the embodiment shown in FIGS. 12 and 13). FIG. 7 depicts a graphical representation of the path created by the rotation of the cam assembly 150 with groove 152. The nonlinear path created ensures that the increase and decrease of the linear velocity of the inner cutter tube 170 is not constant. The cam 150 is a static or immovable component relative to the resector handle or housing. The driver 130 rotates but is longitudinally stationary, and a follower 160, which connects the inner tube 170 to the drive system, both rotates and moves longitudinally. The optional nonlinear path feature results in the maximum translation speed of the cutter tube 170 occurring when the cutting window (see, e.g. FIGS. 12 and 13) being nearly closed, which may increase cutting efficiency.

When the motor 110 is turned on, the drive shaft 112 rotates. The rotation of the drive shaft turns the drive gear 120. The drive gear 120 turns the spur gear 122 in a 1:1 ratio. The spur gear 122 then turns the two planetary gear systems in series to create a gear reduction to meet the desired performance specification.

The inner cutter tube 170 is mounted to the follower which is forced to follow the path created by the groove 152 of cam 150. The result is a longitudinal translational motion of the inner cutter tube 170 while it rotates. The outer cutter tube 190 (FIGS. 12-13) is fixed to the handle.

In certain embodiments, the planetary drive assembly provides the advantage of low noise and vibration since it operates on a single axis. In some preferred embodiments, it also provides increased torque due to gear reduction.

In accordance with the present invention, a second embodiment employing a worm gear drive assembly 200 is shown in FIGS. 8-12. A worm gear drive assembly 200 includes a motor 210, a drive shaft 212 attached at one end to the motor 210 and at the other end to a first spur gear 220 and a worm 230. A worm gear 232 is positioned under the worm 230 and meshes with the threading of the worm. A crank 240 is attached to the worm gear 232 at one end and to a collar 250 at the other end. A second spur gear 222 is positioned below the first spur gear 220 and meshes with the first spur gear 220. The inner cutting tube 270 is connected to the second spur gear 222 through the collar 250.

Actuation of the motor 210 rotates drive shaft 212 which in turn rotates the first spur gear 220 and the worm 230 simultaneously. Rotation of the worm 230 turns the worm gear 232 and rotation of the worm gear 232 creates a longitudinal translational movement (forward and backward movement) of the collar 250 through the attached crank 240 because the crank 240 is attached to the worm gear 232 at a non-centric location 251 on the worm gear 232. At the same time, rotation of the first spur gear 220 turns the meshed second spur gear 222. The second spur gear 222 only rotates around its central axis. Since the inner cutting tube 270 is connected to the second spur gear 222 through the collar 250 and the collar is connected to the worm gear 232 via the crank 240, simultaneous longitudinal translational and rotational movements of the inner cutting tube 270 is achieved.

Figure 8:
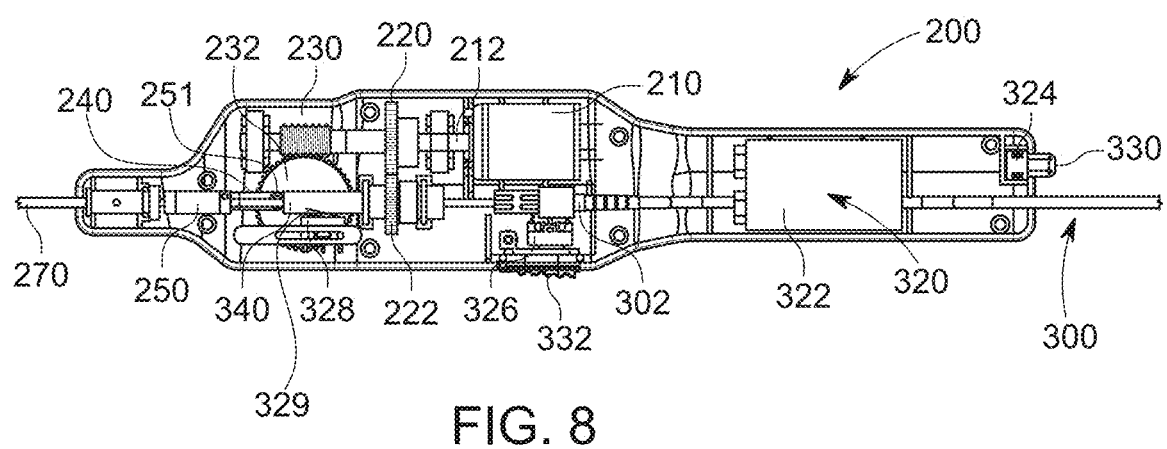
FIG. 8 is a side elevation of an embodiment of the apparatus of the invention.
Figure 9:
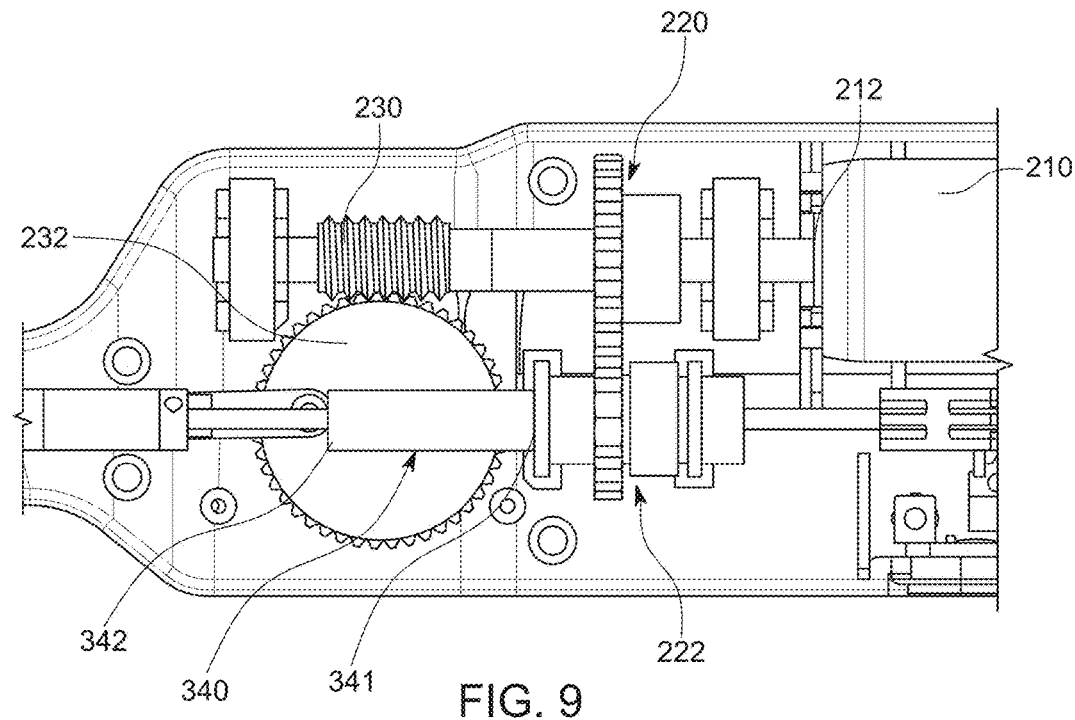
FIG. 9 is a partial side elevation of the embodiment of FIG. 8.
Figure 10:
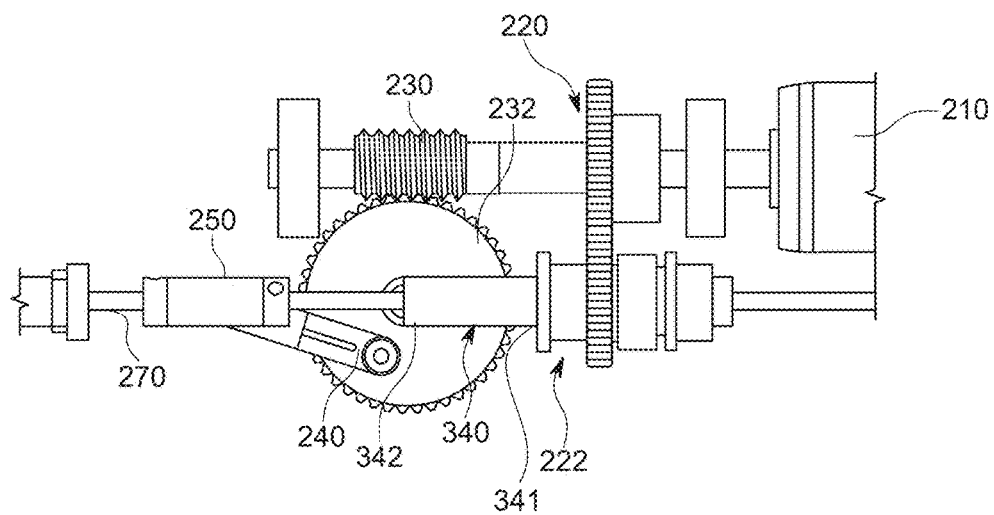
FIG. 10 is side elevation of an embodiment of a gearing arrangement of the invention.
Figure 11:
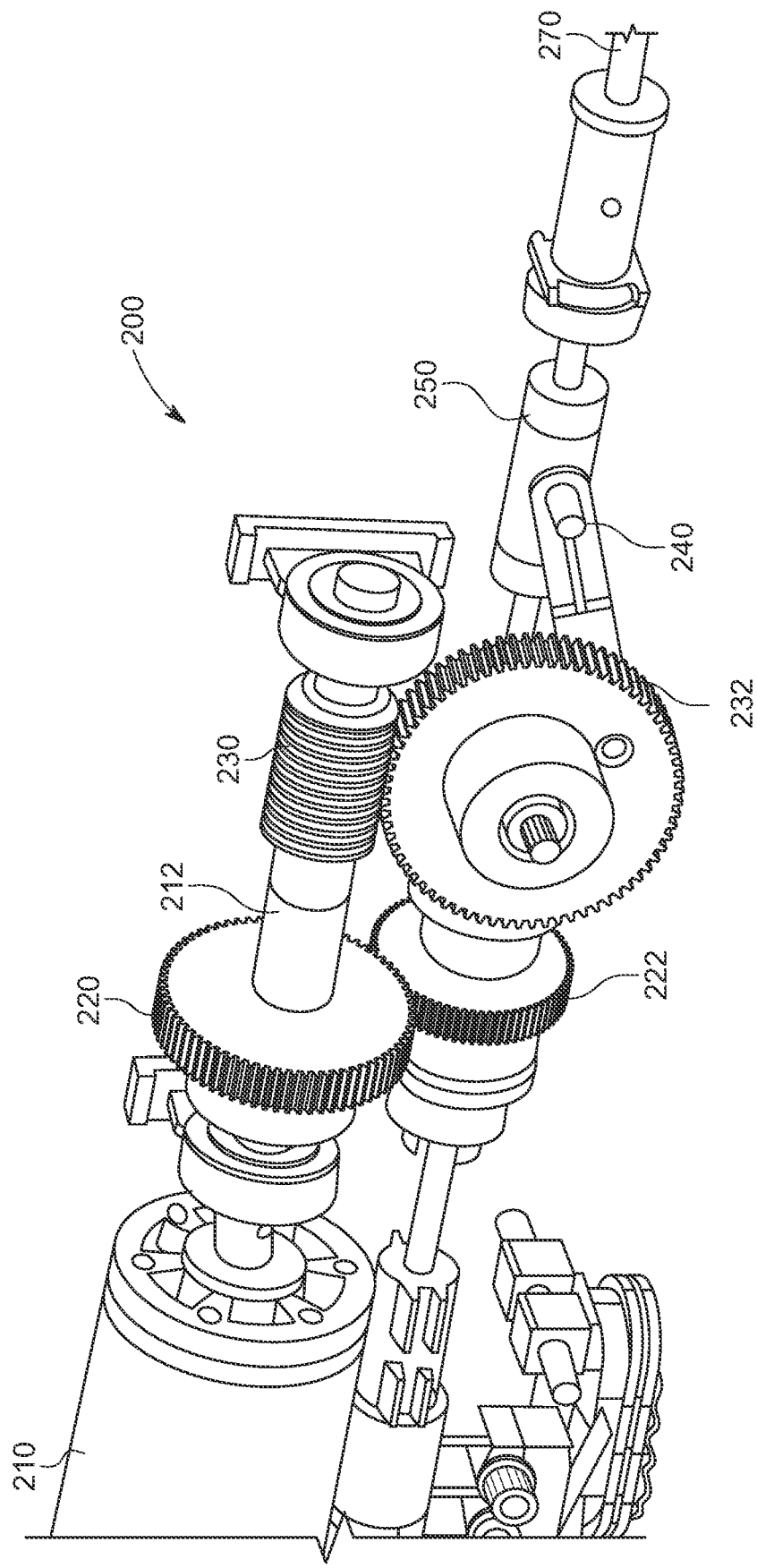
FIG. 11 is a perspective view of an embodiment of a gearing arrangement of the invention.

The worm gear drive system 200, including the motor 210, is energized by a power system 320, best seen in FIG. 8. The system 320 includes a power source 322, three switches 324, 326 and 328, an on/off toggle 330, and an activation button 332. The power source 322 is shown as a standard 9V battery but one skilled in the art will realize that other power sources may be used. The power source is connected to the rest of the system 320 first with the first switch 324. The first switch 324 is operated by the on/off toggle 330 at the base of the handle. This switch 324 connects power from the battery to the rest of the system and prevents activation in the event that the activation button 332 is accidentally depressed.

With the toggle 330 in the on position, current is supplied to the motor via switches 326 and 328. Switch 326 is operated by the activation button 332, which is biased toward the off position and must be held down to connect the power source 322 to the motor 210.

Switch 328 is a safety switch that ensures the inner cutting tube 270 always reassumes the extended position, explained below, when the activation button 332 is released. The safety switch 328 is biased toward an on position and has an actuation lever 329 that opens the switch when depressed. The safety switch 328 is connected in parallel between the power source 322 and the motor 210 with the activation switch 326. A sleeve 340, which includes a first sleeve end 341 and a second sleeve end 342, surrounds the proximal end of the inner tube 270, increasing the diameter thereof. In the fully extended position, the sleeve 340 impinges on the lever 329 of the safety switch 328, placing the switch in the open position, and cutting current to the motor 210.

Because the safety switch 328 and the activation switch 326 are connected in parallel to the motor 210, current is supplied to the motor until both switches 326 and 328 are open. This only occurs when the activation button 332 is released and the sleeve 340 reaches the extended position and depresses the lever 329 of the safety switch 328.

FIGS. 12-13 show the distal end of the device and the interaction between the rotating and reciprocating inner cutting tube 270 and the stationary cutting tube 290. The outer, stationary cutting tube 290 defines a window 292 bordered by a sharpened edge 294. The tube 290 also has a distal end 296. In one embodiment the distal end 296 is closed, as shown in the figures. The window 292 is elongate and terminates prior to the distal end 296. In one embodiment, the window 292 extends around about one half of the circumference of the tube 290, as shown. This maximizes the amount of tissue that can be drawn in while still providing adequate suction and strength to the end of the outer tube 290. The outer tube 290 further has a lumen 198 that runs the length of the tube 290 and carries the inner tube 270 within.

The inner tube 270, as described above, spins on its longitudinal axis and also reciprocates from a retracted position to an extended position. In the retracted position, in at least one embodiment, the inner tube 270 does not appear within the window 292 of the outer tube 290. FIG. 12 shows the inner tube 270 nearly in the retracted position but is extended slightly in order to show the detail of the distal end of the inner tube 270.

In the extended position, shown in FIG. 13, the inner tube 270 is fully extended to the distal end 296 of the outer tube 290 and completely blocks the window 292. The inner tube 270 has a distal end 272 that has a sharp edge 274 and defines a lumen 276. The inner tube 270 has an outer diameter that is slightly smaller than an inner diameter of the outer tube lumen 298 in order to minimize friction between the two tubes, but close enough to slice tissue that gets trapped between the edges 294 of the window 292 and the edge 274 of the distal end 272 of the inner tube 270.

At least the inner tube lumen 276 is operably connected to suction supplied by a suction tube 300 connected to the proximal end of the cutting tube 270 with a connector 302 (FIG. 8). Pathology to be removed is drawn into the window due to the suction applied through the lumen 276 such that the reciprocating and spinning interaction between the inner tube 270 and the outer tube 290 can cut the tissue. When the inner cutting tube 270 is in the extended position shown in FIG. 13, the lumen 276 of the inner cutting tube 270 is blocked by the distal end 296 of the outer tube 290. As explained above, the electrical system 320 ensures that when the activation button 332 is released, the motor 210 is still powered until the inner cutting tube 270 is in the extended position. Thus, when the device is not activated, and the inner tube 270 is in the extended position, the window is blocked ensuring that no tissue is being inadvertently damaged, even if suction remains in the suction tube 300.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A reciprocating drive system for a cutting tube comprising:
   a power source;
   a motor connected to the power source and having a drive shaft extending therefrom;
   a first spur gear attached to the drive shaft;
   a worm connected to the drive shaft;
   a cutting tube adjacent the drive shaft and parallel thereto;
   a second spur gear surrounding the cutting tube and meshed with the first spur gear;
   a worm gear positioned under the worm and meshed therewith such that rotation of the worm around a first axis results in rotation of the worm gear around a second axis perpendicular to the first axis;
   wherein a third axis extending longitudinally through a center of the cutting tube orthogonally intersects the second axis of the worm gear;
   a crank attached at one end to the worm gear and at a second end to a collar attached to the cutting tube;
   a housing including a handle, the housing enclosing the power source, the motor, the first spur gear, the worm, the second spur gear, the worm gear, and the crank;
   the power source being positioned within the handle adjacent to the cutting tube;
   the motor being positioned above the cutting tube and proximally with respect to the first spur gear and the second spur gear;
   wherein rotation of the drive shaft causes rotation of the cutting tube via the first and second spur gears and simultaneously causes reciprocating translation of the cutting tube along a longitudinal axis thereof;
   a sleeve extending distally from the second spur gear and terminating at a location within the housing adjacent the crank and the worm gear;
   wherein the sleeve is fixedly coupled to and extends radially outward from a proximal portion of the cutting tube that is formed integrally with a distal portion of the cutting tube, the proximal portion located within the housing and the distal portion located externally to the housing;
   wherein an end of the sleeve translates across and extends distally beyond a lever of a safety switch to open the safety switch when the cutting tube translates into a distal-most position, the safety switch located entirely below the cutting tube and distal to the first spur gear and the second spur gear, and wherein the cutting tube extends proximally beyond the safety switch toward the second spur gear; and
   wherein the motor cannot receive current from the power source when both the safety switch and a motor activation switch are open.

2. The reciprocating drive system of claim 1, further comprising a first switch connected to a toggle and electrically located between the power source and the motor such that the motor cannot receive current from the power source unless the first switch is closed.

3. The reciprocating drive system of claim 2, wherein the motor activation switch is a second switch connected to an activation button and electrically located between the first switch and the motor such that the motor cannot receive current from the power source unless the first switch and second switches are closed.

4. The reciprocating drive system of claim 3, wherein the second switch is closed by depressing the activation button.

5. The reciprocating drive system of claim 3, wherein the safety switch is a third switch electrically located between the first switch and the motor such that the motor cannot receive current from the power source unless the first switch and at least one of the second and third switches are closed.

6. The reciprocating drive system of claim 1, wherein the drive shaft is positioned above the cutting tube.

7. The reciprocating drive system of claim 1, wherein the worm gear is positioned adjacent to the cutting tube.

8. The reciprocating drive system of claim 1, wherein the first spur gear is positioned above the second spur gear.

9. The reciprocating drive system of claim 1, wherein the safety switch is located between the worm gear and the second spur gear.

10. The reciprocating drive system of claim 9, wherein the motor activation switch is located below the cutting tube proximally to the worm gear and the second spur gear.

11. A tissue resection device comprising:
    a power source;
    a single motor connected to the power source;
    an activation button for activating or deactivating the single motor;

an outer tube having a first lumen, a closed distal end, and a window through a sidewall thereof leading to the first lumen, the window being located proximal of the closed distal end; and, an inner tube within the first lumen and having a second lumen extending between an open distal end and an open proximal end, wherein the open proximal end is connected to a suction source;

a worm gear connected to the inner tube by a crank, wherein the worm gear is configured to rotate about a central axis, and wherein a longitudinal axis of the inner tube orthogonally intersects with the central axis of the worm gear;

a first mechanism connecting the single motor and the inner tube that transfers rotational movement from a drive shaft of the single motor to the inner tube, the first mechanism including a first spur gear attached to the drive shaft and a second spur gear attached to the inner tube, wherein the first spur gear is meshed with the second spur gear;

a housing enclosing the power source, the single motor, the worm gear, and the first mechanism;

a sleeve extending distally from the second spur gear and terminating at a location within the housing adjacent the crank and the worm gear, wherein the sleeve is fixedly coupled to and extends radially outward from a proximal portion of the inner tube so as to increase an outer diameter of the proximal portion of the inner tube, wherein the proximal portion of the inner tube is located within the housing, and wherein the proximal portion is formed integrally with a distal portion of the inner tube located externally to the housing;

a first switch and a second switch electrically connected in series between the power source and the single motor;

a third switch connected in parallel with the second switch between the first switch and the single motor, the third switch comprising a lever positioned entirely underneath the inner tube and distal to the first spur gear and the second spur gear, wherein the inner tube extends proximally beyond the third switch toward the second spur gear, and wherein an end of the sleeve translates across and extends distally beyond the lever to open the third switch when the inner tube translates into a distal-most position;

wherein the inner tube is connected to the single motor such that when the single motor receives current from the power source, the inner tube rotates and reciprocates simultaneously within the outer tube; and, wherein the inner tube is configured to fully block the window when the activation button is released.

12. The device of claim 11, further comprising a second mechanism connecting the single motor and the inner tube that converts rotational movement from a drive shaft of the single motor into reciprocating movement of the inner tube.

13. The device of claim 12, wherein the second mechanism comprises the worm and the worm gear, the worm being attached to the drive shaft, and the worm gear being attached to the inner tube via the crank.

14. The device of claim 13, wherein the crank has a first end attached to the worm gear at a non-centric location and a second end attached to a collar on the inner tube.

15. The device of claim 13, wherein the worm gear is positioned under the worm.

16. The device of claim 15, wherein the worm gear is positioned adjacent to the inner tube.

17. The device of claim 11, wherein the second axis of the worm gear orthogonally intersects the sleeve when the inner tube is in the distal-most position.

18. The device of claim 11, wherein the second switch is located below the inner tube adjacent a connection of the inner tube to a suction source.

\* \* \* \* \*